(12) United States Patent
Baz

(10) Patent No.: US 11,311,069 B2
(45) Date of Patent: Apr. 26, 2022

(54) FACE SHIELD AND ITS ASSEMBLY METHOD

(71) Applicant: DNA Gadgets LLC, Las Vegas, NV (US)

(72) Inventor: Eduardo Jauregui Baz, Huixquilucan (MX)

(*) Notice: Subject to any disclaimer, the term of this patent is extended or adjusted under 35 U.S.C. 154(b) by 202 days.

(21) Appl. No.: 16/837,792

(22) Filed: Apr. 1, 2020

(65) Prior Publication Data

US 2021/0307446 A1    Oct. 7, 2021

(51) Int. Cl.
*A41D 13/11*       (2006.01)
*A42B 3/20*        (2006.01)
*A61F 9/02*        (2006.01)

(52) U.S. Cl.
CPC ............. *A42B 3/20* (2013.01); *A41D 13/1184* (2013.01); *A61F 9/02* (2013.01)

(58) Field of Classification Search
CPC .......... A41D 13/1184; A42B 3/20; A61F 9/02
See application file for complete search history.

(56) References Cited

U.S. PATENT DOCUMENTS

| | | | | |
|---|---|---|---|---|
| 2,774,970 A * | 12/1956 | Rudolf | ............... | A41D 13/1161 2/9 |
| 4,945,573 A * | 8/1990 | Landis | ............... | A41D 13/1184 2/9 |
| 5,206,956 A * | 5/1993 | Olson | ................ | A41D 13/1184 2/13 |
| 5,337,419 A * | 8/1994 | Russell | ............. | A41D 13/1184 2/9 |
| D354,588 S | 1/1995 | Russell | | |
| 5,440,760 A * | 8/1995 | Highsmith | ......... | A41D 13/1184 2/9 |
| 5,765,223 A * | 6/1998 | McCausland | ...... | A41D 13/1184 2/9 |
| 5,983,390 A * | 11/1999 | Desy | .................. | A41D 13/1161 128/858 |
| 9,532,617 B2 * | 1/2017 | Miller | ................ | A41D 13/1184 |
| D853,656 S * | 7/2019 | Martin | ............... | A41D 13/1184 D29/110 |
| 2012/0047614 A1 * | 3/2012 | Choi | .................. | A41D 13/1184 2/9 |
| 2016/0030779 A1 * | 2/2016 | Twu | .................... | A41D 13/1184 128/202.13 |

* cited by examiner

*Primary Examiner* — Tajash D Patel
(74) *Attorney, Agent, or Firm* — James R. McDaniel

(57) ABSTRACT

The present invention refers to a face shield for the protection of user's eyes and face in case there s accidental exposure to infectious, hazardous, and undesired substances, chemicals, powders, liquid spray, aerosols, and particles. More specifically, the invention refers to a protective barrier for workers in the health industry, laboratory personnel, dentists, dermatologists, beauty parlors, spas, dialysis clinics, tattoo artists, janitorial personnel, artists, and workshops of varying types, for protection against accidental exposure to infectious and/or hazardous and potentially toxic materials, as well as harmful airborne particles.

10 Claims, 3 Drawing Sheets

FACE SHIELD AND ITS ASSEMBLY METHOD

TECHNICAL OF THE INVENTION

This invention refers to a face shield for the protection of a user's eyes and face in case there is accidental exposure to infectious, hazardous, and undesired substances, chemicals, dust, liquid spray, aerosols, and/or particles, More specifically, the invention refers to a protective harrier for workers in the health industry, laboratory personnel, dentists, dermatologists, beauty parlors, spas, dialysis clinics, tattoo artists; anitorial personnel, artists, and workshops of varying types, for protection against accidental exposure to infectious and/or hazardous and potentially toxic materials, as well as harmful airborne particles.

BACKGROUND OF THE INVENTION

Healthcare professionals work with infectious diseases patients, which puts them at risk of suffering an illness. For example, there have been documented cases of Coronavirus transmission to healthcare professionals and individuals who care for patients and the elderly, which is an alarming concern for authorities and general population.

Additionally, there is a higher risk of infection for surgeons and personnel in the operating Room (OR) if saliva, blood, or other body fluids spray on the eyes and face, especially in cases involving open wounds, during the procedures.

Regarding the prevention of Coronavirus transmission in healthcare environments, there is a growing concern regarding the protection of the eyes and face especially in the event that saliva, blood, and/or other body fluids from the patient spray onto the surroundings, such as the aerosols produced by patients when they cough. For this reason, healthcare professionals and laboratory workers must use eye protection; however, regular shields are not sufficient protection. Currently, there are face shields-like the one disclosed in U.S. Pat. No. USD354,588, issued on Jan. 17, 1995, which completely covers the face but exhibits issues regarding its robustness, the large amount of assembly parts, and excess weight. The present invention solves these issues.

One goal of the present invention is to provide a face shield for the protection of a user's eyes and face in the event of accidental exposure to infectious, hazardous, and undesired substances, forming a barrier against organic materials and hazardous airborne particles, and which prevents particles from making impact on the eyes and face, provides insulation against powder, saliva, spray from chemical products, and other substances.

Another goal of the invention is to provide a face shield for the care of healthcare and laboratory workers, as well as many other professions, against accidental exposure to body fluids of infected patients, spray from chemical products, protection against powder, pollen, and the impact of particles.

An additional goal of the invention is to provide a low-cost face shield fbr healthcare workers as well as laboratory professionals and personnel, dentists, dermatologists, who are subject to accidental exposure to infectious fluids.

Another goal of the invention is to provide an ultra-light and comfortable face shield for a wide variety of workers who may be exposed to infectious, hazardous, and undesired substances.

Yet another goal of the invention is to provide an ultra-light disposable face shield which is easily formed from a flat packaged preform and can be used over traditional eyeglasses and face masks.

Yet another goal of the invention is to overcome current logistical issues regarding handling and transportation and storage in sales locations, as it does not occupy much space given its thinness and light weight.

The advantages of the invention will be made evident in the detailed description of the preferred embodiment of the invention and the accompanying illustrations.

DESCRIPTION OF TILE INVENTION

DETAILED DESCRIPTION OF THE INVENTION

Figure 1:
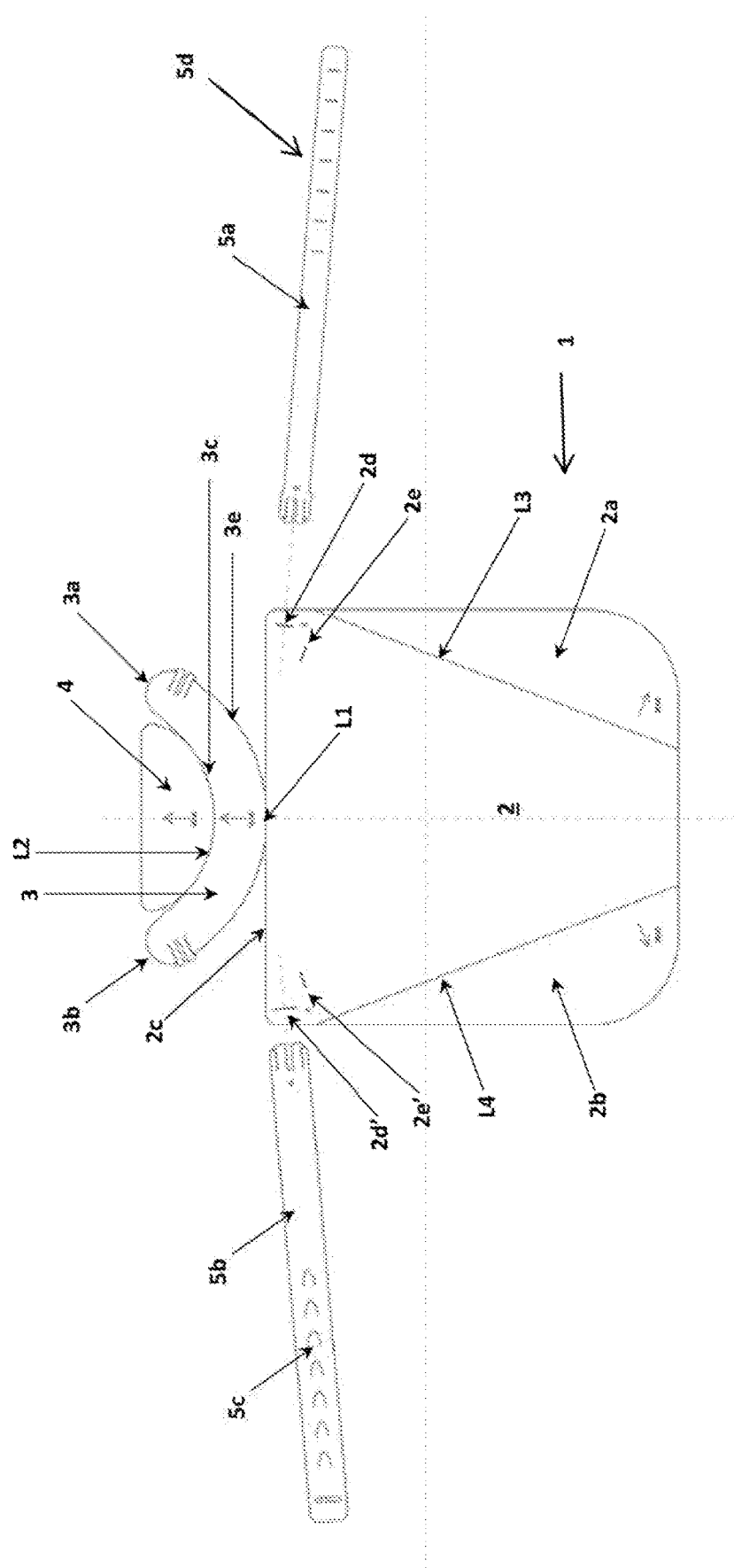
FIG. 1 illustrates a view of the preform of the present invention for the assembly of the face shield.
Figure 2:
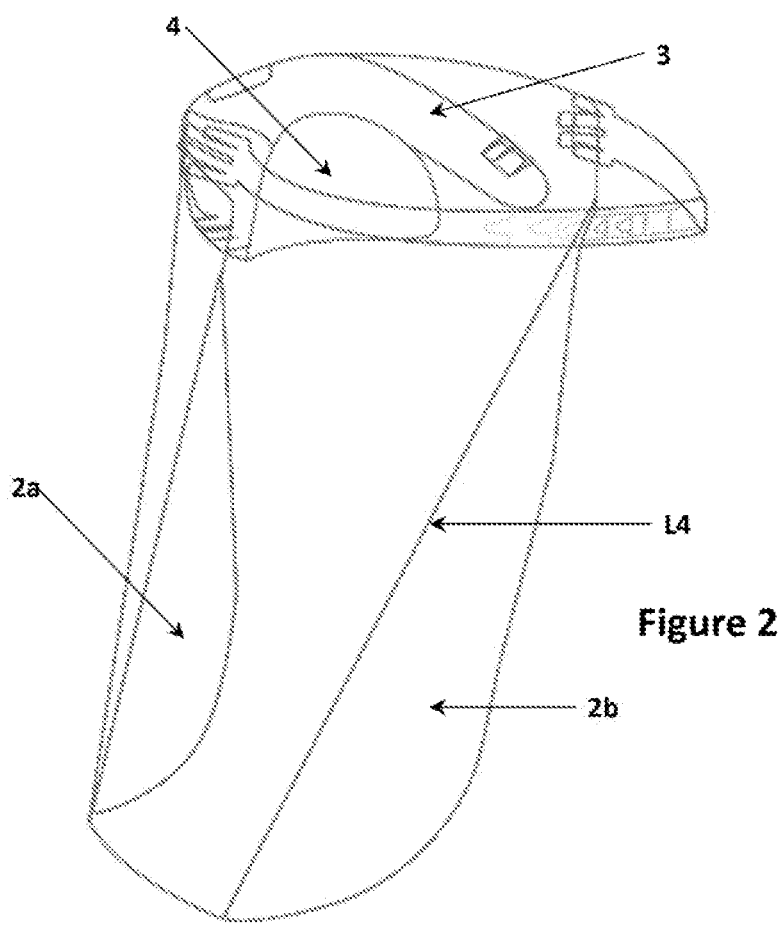
FIG. 2 illustrates a perspective view of the assembled face shield.
Figure 3:
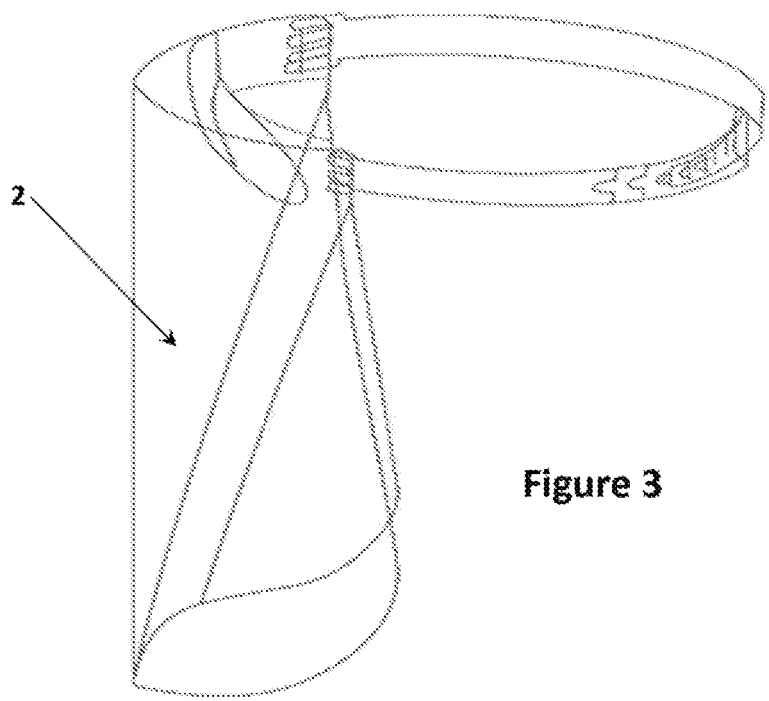
FIG. 3 illustrates a second perspective view of the assembled face shield.
Figure 4:
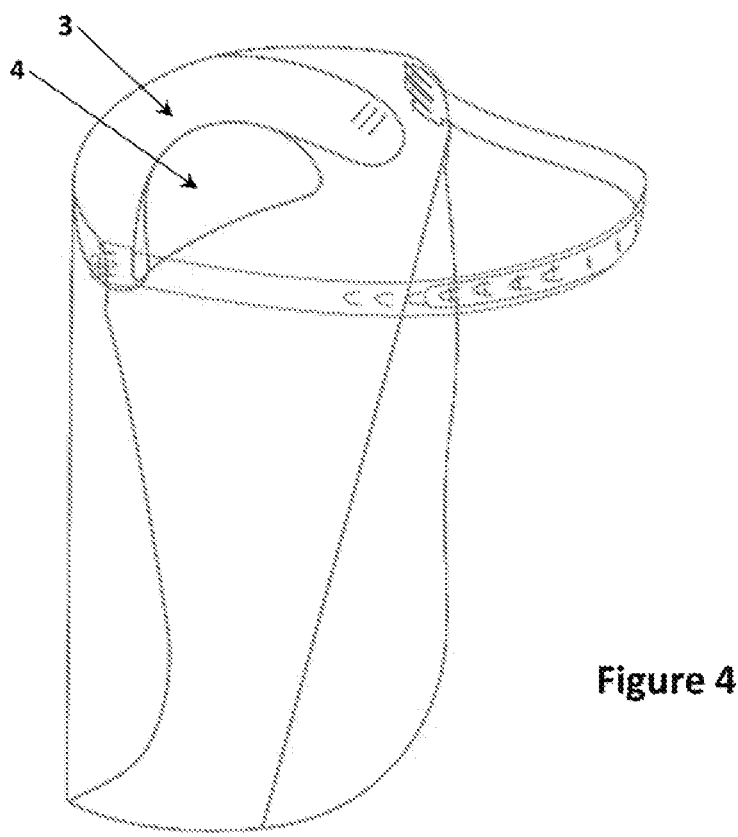
FIG. 4 illustrates a third perspective view of the assembled face shield.

The invention which is the object of this patent application is a face shield preform (1), the face shield obtained after assembling the preform, and the assembly method.

The face shield which in the present invention is comprised of a preform (1) made of transparent material with a frontal protective panel (2) a lateral protective panel (2a), a second lateral protective panel (2h), with two upper side grooves (2d), two diagonal grooves (2e) located near each of the upper side grooves (2d), and an upper edge (2c).

Figure 5:
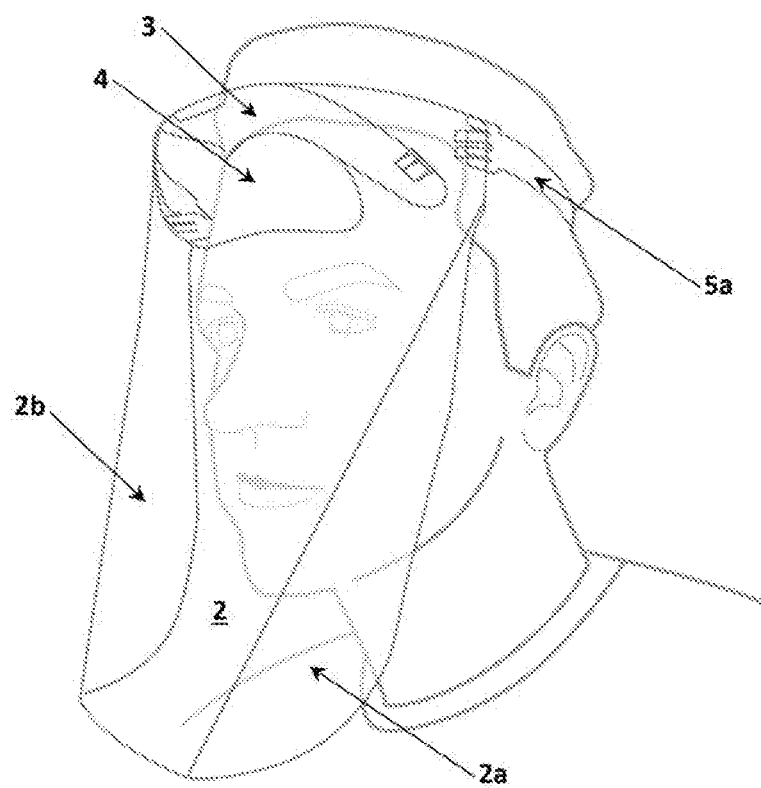
FIG. 5 illustrates a perspective view of the face shield as it protects the user's face.

The first lateral protective panel (2a) is made in one piece together with the frontal protective panel (2) connected together by a third weakness line (L3); additionally, the second lateral protective panel (2b) is made in one piece together with the frontal protective panel (2) connected together by a fourth weakness line (L4). The function of the third weakness line (L3) and the fourth weakness line (L4) is to facilitate folding over the weakness lines to position the lateral portions appropriately around the user's face and provide the most efficient protection against contamination from the sides of the face shield. The dimensions of the face shield ensure that the user's entire face is protected, as can be seen in FIG. 5.

The preform (1) used to assemble the face shield is preferably made of PETG material, which are polyethylene terephthalate glycol co-polyester extrusion plates, a semi-rigid and transparent material. Although the preferred embodiment of the face shield of the present invention is manufactured from PETG material, the face shield is not limited only to the PETG material, as it can be manufactured from other materials such as PET, PVC, Polycarbonate, HIPS, Mylar, and others.

In order to provide a gap, between the frontal protective panel (2) and the user's face once the face shield is assembled, there is a separation segment (3), which is of a curved configuration, curving upward with winged endpoints (3a, 3b), in such a way as to form an internal hollow (3c), wherein each endpoint wing (3a, 3b) of the separating segment (3) has an attaching device which connects to the diagonal grooves (2e), and is joined to a portion of the upper edge (2c) of the transparent material preform by the first weakness line (L1). This structural configuration demonstrates that the frontal protective panel (2) and the separating segment (3) are made in one piece.

The attaching device of the endpoint wings (3a, 3b) which connects to the diagonal grooves (2e) may be any joining device which can be attached and detached. In the illustrated embodiment, which is not exclusive, an attachment method comprised of two latching ends can be seen, where the separation between the latching ends allows inward flexibility to insert them in the diagonal grooves (2e) of the frontal protective panel (2).

As shown in FIG. 1, the inclination of the diagonal grooves (2e) of the frontal protective panel (2) helps to adopt a form appropriate to the user's face, along with an exterior border (3e) of the separating segment (3) when the exterior border (3e) is attached to the back surface of the frontal protective panel (2).

The invention furthermore comprises a forehead supporting segment (4) with a semicircular configuration which joins a portion of the internal hollow (3c) of the separating segment (3) by a second weakness line (L2), With this structural configuration, it can be observed that the frontal protective panel (2), the separating segment (3), and the forehead supporting segment (4) are made in one piece.

The function of the forehead supporting segment (4) is to be placed over the forehead of the user once the face shield is assembled.

The second weakness line (L2) helps to fold over thereof to make the forehead supporting segment (4) into a form appropriate to the user's face, with respect to the separating segment (3).

So that the user may wear the face shield over his/her head safely and comfortably, supporting means are provided, such as a supporting band (5a), a second supporting band (5b), where the supporting band (5a) is comprised of an attachable end, slots (5d), and a second free end, where the attachable end is freely attached to an upper lateral groove (2d) of the frontal protective panel (2), and the second supporting band (5b) comprises an attachable end, tabs (5c), and a free end, where the attachable end is freely attached to an upper lateral groove (2d') of the frontal protective panel (2), in such a way that the free ends of the first supporting band (5a) and the second supporting band (5b) can be attached and adjusted to adapt to the dimensions of the user's head.

For the purpose of allowing the face shield to be adaptable to different users' head dimensions, there are tabs (5c) and slots (5d) for adjusting the dimensions along the supporting band (5a) and second supporting band (5b). In particular, the supporting bands (5a and Sb) will be placed around the head of the user, Once the desired size of the supporting bands (5a and 5b) has been determined, tabs (5c) will interact with slots (5d) on order to retain supporting bands (5a and 5b) on the head of the user.

The present invention also provides a method for assembling a face shield from the preform; the method comprises the following steps:
  a) Fold the lateral protective panel (2a) backwards, based on the user's preference, along the length of the weakness line (L3);
  b) Fold the lateral protective panel (2b) backwards, based on the user's preference, along the length of the weakness line (L4);
  e) Fold the separating segment (3) 90 degrees backwards, along the length of the weakness line (L1);
  d) Fold the frontal support (4), starting from the middle, in order to form a curve on the weakness line (L2), this step forms the final shape of the separating segment (3)
  e) Assemble the attaching device of the endpoint wing (3a) on the diagonal groove (2e);
  f) Assemble the attaching device of the endpoint wing (3b) on the diagonal groove (2e');
  G) Assemble the supporting band (Sb) on the upper side groove (2d') with the attaching device from the back side of the face shield;
  h): Assemble the supporting band (5a) on the upper side groove (2d) with the attaching device from the back side of the face shield;
  i) insert the supporting band (5a) into the end of the supporting band (5b);
  j) Raise a tab (5c) in order to adjust the dimensions so that the supporting bands (5a) and (5b) can be used to fit to the head size of the user;
  k) Slide the two supporting bands (5a and 5b) to obtain the desired diameter and fix the raised tab (5c) into the slots (5d) (means for adjusting the dimensions).

Having sufficiently described my invention, which I consider novel, I claim as my exclusive property the following:

1. A preform of transparent material to assemble a face shield, which comprises:
   a frontal protective panel (2), a lateral protective panel (2a), a second lateral protective panel (2b), wherein the frontal protective panel includes two upper side grooves (2d), two diagonal grooves (2e) located adjacent to each of the upper side grooves (2d), and an upper edge (2c);
   a separating segment (3) having a curved configuration, wherein the separating segment curves upwardly and includes winged endpoints (3a, 3b), wherein the winged endpoints form an internal hollow (3c) such that each endpoint wing (3a, 3b) includes an attaching device which connects to each of the diagonal grooves, and wherein the separating segment (3) is operatively connected to a portion of the upper edge (2c) through a first weakness line (L1); and
   a forehead supporting segment (4) having a semicircular configuration, wherein the forehead supporting segment is operatively connected to a portion of the internal hollow of the separating segment (3) through a second weakness line (L2).

2. The preform, according to claim 1, characterized in that the preform is manufactured of any transparent and semi-rigid material, such as PETG and PET, PVC, Polycarbonate, HIPS, Mylar, and others.

3. The preform, according to claim 1, characterized in that the preform further comprises:
   a supporting band (5a) having an attachable end and a free end; and
   a second supporting band (5b) with an attachable end and a free end.

4. The preform, according to claim 1, characterized in that the first lateral protective panel (2a) is made in one piece together with the frontal panel protector (2) connected by a third weakness line (L3).

5. The preform, according to claim 1, characterized in that the second lateral protective panel (2b) is made in one piece together with the frontal panel protector (2) connected, by a third weakness line (L3).

6. A face shield, which comprises:
   a frontal protective panel (2), a lateral protective panel (2a), a second lateral protective panel (2b), wherein the frontal protective panel includes two upper side grooves (2d), two diagonal grooves (2e) located adjacent to each of the upper side grooves (2d), and an upper edge (2c);
   a separating segment (3) having a curved configuration, wherein the separating segment curves upwardly and includes winged endpoints (3a, 3b), wherein the winged endpoints form an internal hollow such that each endpoint wing (3a, 3b) includes an attaching device which connects to each of the diagonal grooves, and wherein the separating segment (3) is operatively connected to a portion of the upper edge (2c) through a first weakness line (L1)
   a forehead supporting segment (4) having a semicircular configuration, wherein the forehead supporting segment is operatively connected to a portion of the internal hollow of the separating segment (3) through a second weakness line (L2); and
   a plurality of supporting, devices (5a, 5b) attached to the upper side grooves (2d), wherein the plurality of supporting devices is used to adapt to the user's head and support the Pace shield on the user's head.

7. The face shield, according to claim 6, characterized in that the supporting means comprises:
   a supporting band (5a) with an attachable end and a free end, where the attachable end is freely attached to an upper side groove (2d) of the frontal protective panel (2); and
   a second supporting band (5b) with an attachable end and a free end, where the attachable end is freely attached to an upper side groove (2d) of the frontal protective panel (2).

8. The face shield, according to claim 6, characterized in that the attaching device of the end wings (3a, 3b) of the separating segment (3) that attaches to the diagonal grooves (2e) can be any joining device which can be attached and detached.

9. The face shield in accordance with claim 6, characterized, in that die attaching device is comprised of two latching ends, where the separation between the latching ends allows inward flexibility to insert the latching ends in the diagonal grooves (2e) of the frontal protective panel (2).

10. A method for assembling a face shield, which comprises the following stages:
   a) fold a first lateral protective panel (2a) backwards, based on a user's preference, along a length of a first weakness line L3);
   b) fold a second lateral protective panel (2b) backwards, based on the user's preference, along a length of a second weakness line (L4);
   c) fold a separating segment (3) 90 degrees backwards, along a length of a third weakness (L1);
   d) fold a frontal support (4), starting from a middle of the frontal support, in order to form a curve along a fourth weakness line (L2) in order to form a final shape of the separating segment (3)
   e) attach a first end wing (3a) of the separating segment into a first diagonal groove (2e) in a front protective panel;
   f) attach a second end wing (3b) of the separating segment into a second diagonal groove (2e) in the front protective panel;
   g) attach a supporting band (5b) into a first upper side groove in the front protective panel from a back side of the front protective panel;
   h) attach a second supporting band (5b) into a second upper side groove in the front protective panel from a back side of the front protective panel;
   i) insert the first supporting band (5a) into an end of the second supporting b (5b);
   j) raise a tab (5c) on the second supporting band; and
   k) slide the two supporting bands together in order to obtain a desired diameter and connect the first supporting and to the second supporting ban through the use of the tab and a slot located on the first supporting band.

* * * * *